United States Patent [19]

Molina

[11] Patent Number: 4,932,987
[45] Date of Patent: Jun. 12, 1990

[54] EXTRA CORPOREAL AIR ELIMINATOR

[76] Inventor: Jorge Molina, 1301 E. Tarrent Rd., Grand Prairie, Tex. 75050

[21] Appl. No.: 356,846

[22] Filed: May 25, 1989

[51] Int. Cl.$^5$ .............................................. B01D 19/00
[52] U.S. Cl. ...................................... 55/159; 55/204; 55/487; 210/304; 210/436
[58] Field of Search ........................ 55/159, 204, 487; 210/304, 436

[56] References Cited

U.S. PATENT DOCUMENTS 4,490,254  12/1984  Gordon et al. ..................... 210/436
4,806,135  2/1989   Sipass ............................... 55/459.1

Primary Examiner—Bernard Nozick
Attorney, Agent, or Firm—Ross, Howison, Clapp & Korn

[57] ABSTRACT

An arterial air eliminator includes an upper housing (10) and a lower housing (12). A first internal chamber (16) is formed adjacent the interior sides of the housing with an inlet tube (18) disposed in the upper end thereof. A purge outlet (20) is provided at the upper end of the air eliminator with a filter element (32) defining an interior chamber (24). Fluid flows into the inlet (18) and then through the filter (32) to an interior chamber (34) and out an outlet tube (36) on the lower end of the housing. The filter element (32) has a bubble point that is graduated from the top to the bottom such that the bubble point on the upper end is large relative to the bubble point on the lower end thereof. The microbubbles which exist in the fluid entering the inlet tube (18) are not passed through the upper end of the filter (32) and are purged to the outlet (20).

6 Claims, 3 Drawing Sheets

U.S. Patent  Jun. 12, 1990  Sheet 1 of 3  4,932,987
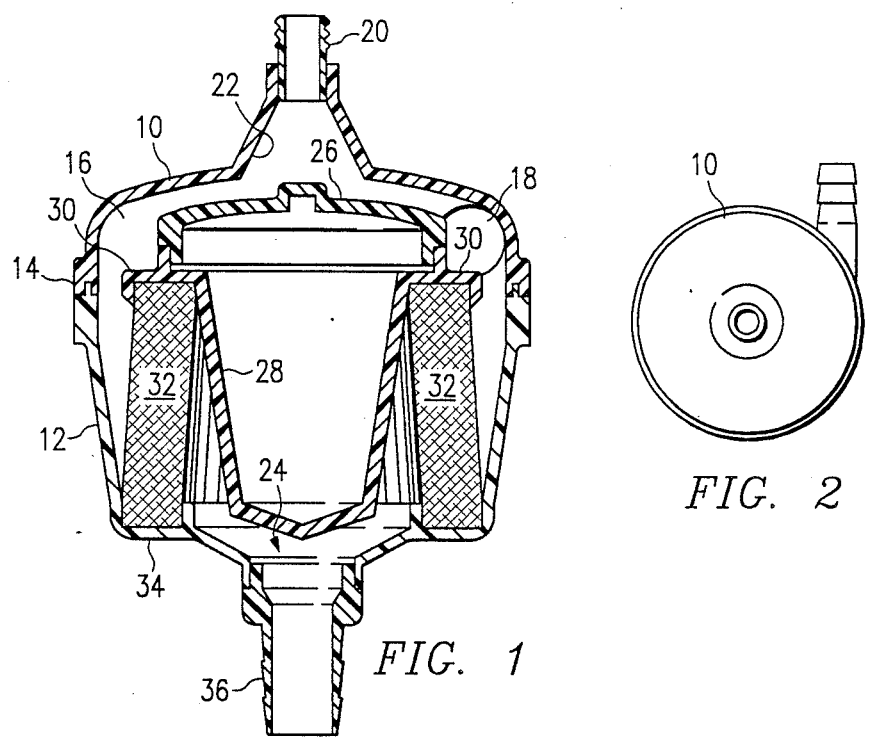
FIG. 1
FIG. 2
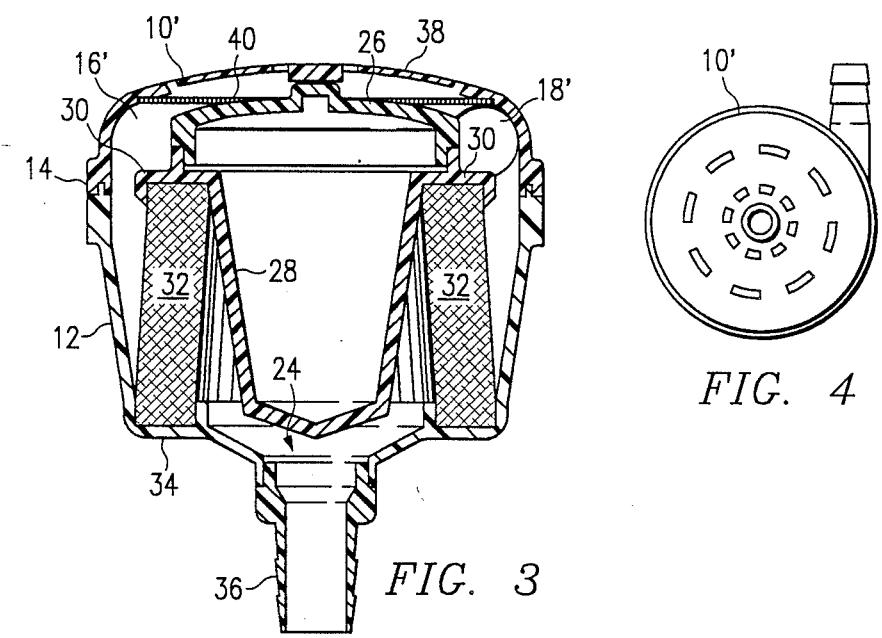
FIG. 3
FIG. 4

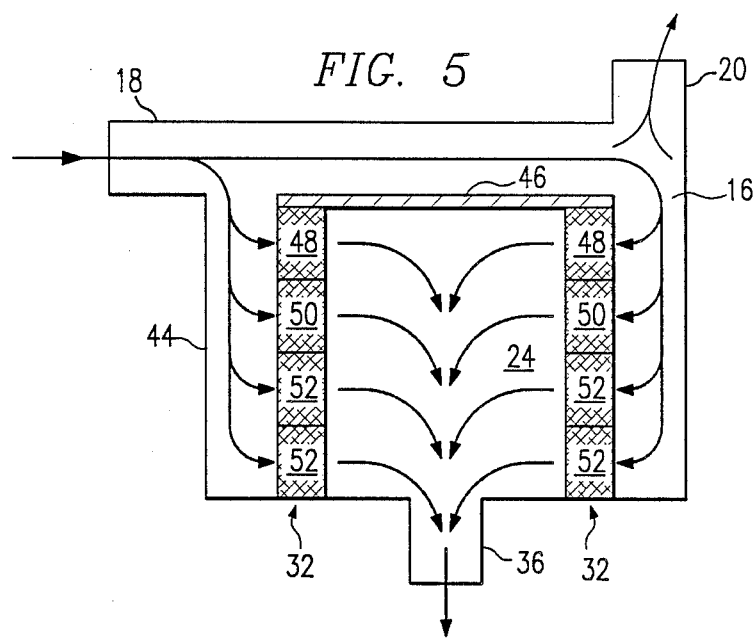
FIG. 5
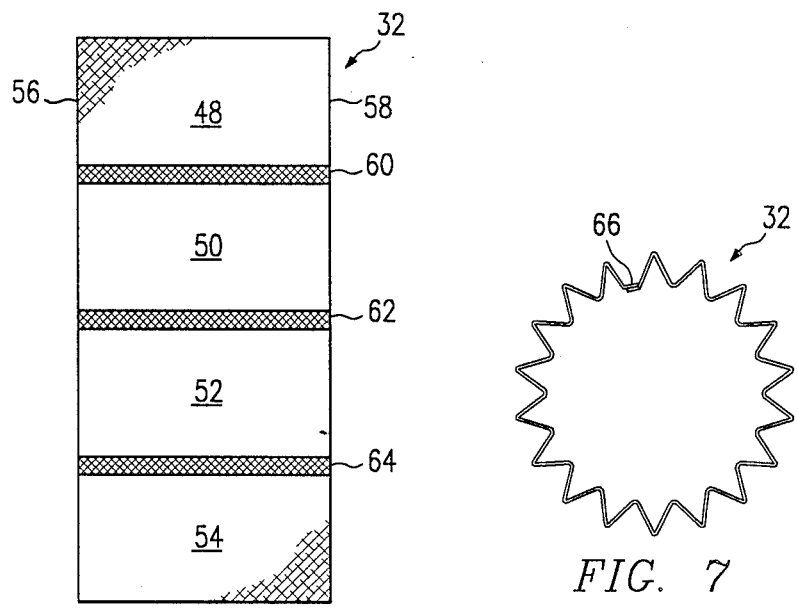
FIG. 6
FIG. 7

EXTRA CORPOREAL AIR ELIMINATOR

TECHNICAL FIELD OF THE INVENTION

The present invention pertains in general to blood filters, and more particularly, to a filter utilized to eliminate air from an extracorporeal filtration device.

BACKGROUND OF THE INVENTION

Filtration of blood has been utilized in the past with cardio-pulmonary bypass techniques to remove contaminants from the blood that may in some way alter the blood, which may eventually result in damage to the perfused tissue. It has been shown that some of these problems are due to the blood oxygenators that produce microemboli which is a result of the proportion at which the oxygen and the blood were mixed.

To remove the microemboli, disposable filters have been utilized. Examples of these are those described in U.S. Pat. Nos. 3,701,433 and 3,696,932, both issued to Pall Corporation. In these types of disposable filters, oxygenated blood enters a first chamber which has a cylindrical filter disposed therein. The interior of the cylindrical filter is sealed off from the first and outer chamber and then a conduit interfaced with the interior of the filter for allowing blood to exit. The filter filters out the gas and microemboli, which gas is then purged from a vent or from a self-venting device. Therefore, surges, entrained microbubbles or inadvertent air boluses can be removed even at high flow rates.

One disadvantage to previous disposable filters is the pore size on the filters and the maximum flow rate therethrough. If the flow rate is increased, the filter will still filter out the undesired contaminants and air microbubbles, but damage may occur to the blood. Therefore, a given filter has an intrinsic maximum available flow rate. In order to increase flow rates, it is necessary to increase the pore size which can have a deleterious effect in that it may not filter out all particles. Therefore, there exists a need for a disposable filter that will maintain the filtration level while allowing an increased flow rate without altering the blood.

SUMMARY OF THE INVENTION

An air eliminator for eliminating air from blood includes a cylindrical outer housing having an upper end and a lower end. An inlet is formed in the upper end of the outer housing and an outlet is formed in the lower end of the outer housing. An interior housing disposed in the outer housing separates the inlet from the outlet to form a first interior chamber for receiving fluid from the inlet and a second interior chamber for outputting fluid to the outlet. The interior housing has at least one substantially vertical surface between the first and second interior chambers, the surface having an upper and a lower end. A filter section is formed on a portion of the substantially vertical surface for allowing fluid to flow therebetween the first and second interior chambers. The filter section has a pore size that increases from a predetermined minimum size at the upper end of the filter section to a predetermined maximum size at the lower end of the filter section. A purge mechanism is provided for eliminating a portion of the fluid and/or air in the upper end of the outer housing.

In yet another aspect of the present invention, the interior housing is cylindrical in shape with an upper sealed end. The peripheral surfaces of the lower end of the cylindrical outer wall thereof form a seal with the lower end of the outer housing such that the outlet is in communication with the interior of the cylindrical housing. The interior of the cylindrical housing forms the second interior chamber. The filter section is cylindrical in shape and disposed about the outer wall of the cylindrical inner housing.

In a yet further aspect of the present invention, the filter section is pleated wherein the outer surface thereof is tapered downward and outward from the cylindrical walls of the interior cylindrical housing. The filter section is configured as a plurality of strips of filter material having progressively increasing pore sizes. Each of the strips has a lower peripheral edge and an upper peripheral edge with the lower peripheral edge of each of the filter strips adhered to the upper peripheral edge of the next adjacent one of the filter strips having a sequentially larger pore size.

BRIEF DESCRIPTION OF THE DRAWINGS

For a more complete understanding of the present invention and the advantages thereof, reference is now made to the following description taken in conjunction with the accompanying Drawings in which:

FIG. 1 illustrates a cross-sectional view of the air eliminator of the present invention;

FIG. 2 illustrates a top view of the air eliminator of FIG. 1;

FIG. 3 illustrates a cross-sectional view of an alternate embodiment of the present invention;

FIG. 4 illustrates a top view of the alternate embodiment of FIG. 3;

FIG. 5 illustrates a diagrammatic view of the filter illustrating the partitioned pore sizes;

FIG. 6 illustrates a view of the expanded membrane;

FIG. 7 illustrates a top view of the pleated configuration of the membrane;

DETAILED DESCRIPTION OF THE INVENTION

Figure 8:
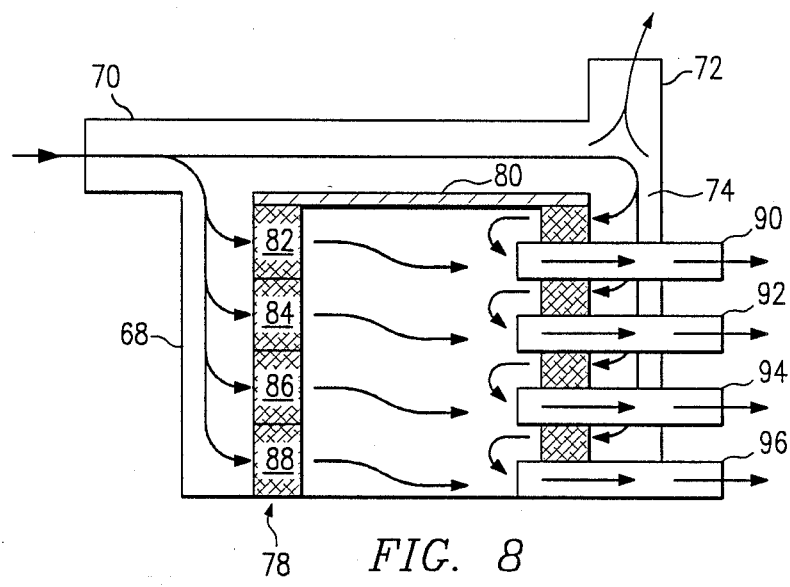
FIG. 8 illustrates a diagrammatic, cross-sectional view of an alternate embodiment of the present invention with taps to each of the chambered portions of the partitioned membrane.

Referring now to FIG. 1, there is illustrated a cross sectional view of the air eliminator of the present invention. The air eliminator is comprised of a two-part molded member having a top 10 and a bottom 12. The top and the bottom are joined at a seam 14 to form an interior chamber 16 therein. The upper portion 10 and lower portion 12 form a housing that is typically formed from thermoplastic materials, including such materials as polyvinyl chloride-vinylide chloride copolymers, polymethyl methacryalate, polystyrene, polyamides, etc.

The housing is polarized such that it has a vertical longitudinal axis that is perpendicular to the general plane of the seam 14 and also perpendicular to the top portion 10. For reasons that will be described hereinbelow, the housing is disposed such that the longitudinal axis is always vertical. The upper housing 10 has an inlet 18 formed therein that is essentially perpendicular to the longitudinal axis and offset to the perpendicular axis such that when fluid enters, it will swirl around the peripheral edges of the interior chamber 16. An upper purge outlet 20 is provided in the upper housing 10 and centrally disposed therewith. The outlet 20 is disposed on a frusto-conical protrusion 22 from the upper housing 10 such that tapered surfaces are provided that taper inward and outward toward the outlet 20 from the interior chamber 16. The purpose of this will be described hereinbelow.

An interior chamber 24 is formed within the chamber 16. The interior chamber 24 is defined by an interior housing having an upper sealed portion 26 and a lower supporting wall 28 that also functions to displace fluid from the interior chamber 24. The lower wall 28 is cylindrical in shape and has at the upper and outer peripheral surface thereof an annular slot 30. The annular slot 30 is operable to receive one end of a cylindrical filter section 32. The other end of the cylindrical filter section 32 is disposed in an annular slot 34 in the lower end of the lower housing 12. The filter section 32 is disposed such that it completely separates the interior chamber 24 from the chamber 16 and all fluid is therefore required to pass through the filter section 32 passing from the chamber 16 into the interior chamber 24. The interior chamber 24 is disposed directly over an outlet tube 36 on the lower end of the lower housing 12 and centrally disposed with respect to the annular slot 34. Therefore, the outlet tube 36 only communicates with the interior chamber 24. A top view of the structure of FIG. 1 is illustrated in FIG. 2.

In operation, fluid enters the upper housing 10 and the interior chamber 16 at the upper end thereof through the inlet tube 18. It circulates in the upper end thereof and then passes downward through the filter section 32. Filter section 32 has a predetermined pore size which will selectively allow fluid and gas to flow therethrough. Particulate matter and air bubbles of a size too large to pass through the filter section 32 will remain in the chamber 16 exterior to the surface of the filter section 32. Air bubbles that do not pass through filter 32, for example, will tend to rise upward toward the frusto-conical protrusion 22 and out the purge tube 20, due to the lower density thereof. Therefore, the purge tube 20 will remove a portion of the fluid in the chamber 16 which portion will have a higher concentration of the larger particulate pattern that is selectively rejected by the filter section 32 than the interior chamber 24.

The filter section 32 is configured such that the outer wall thereof tapers downward and outward. This is to allow air bubbles and the such to rise upward off the surface of the filter section 32. In this manner, air bubbles will tend to rise upward at a faster rate. As will be described hereinbelow, the bubble point in the filter section 32 is graduated from a large bubble point at the upper end thereof to a smaller bubble point at the lower end thereof. Bubble point is defined as the measure of the amount of air pressure required to force liquid from the largest wetted pore of a membrane. This serves as an index of pore size and rates the filter's ability to serve as a particle barrier and to inhibit the passage of air bubbles. The bubble point rating is determined when the largest pore yields a bubble; the larger the pore, the less pressure required to form the bubble. Bubble point is expressed in units of pounds/square inch (psi) for membranes. A portion of the fluid disposed at the upper end of the housing will not pass through the upper end of the filter section 32. This portion of the fluid, which contains particulate matter and associate gas bubbles, will be purged through the outlet 20. However, the higher density fluid with the larger particulate matter and the absence of gas bubbles will fall to the lower end of the housing and pass through the larger pores with an associated lower bubble point in the lower end of the filter section 32. Therefore, low density particulate matter having a size larger than the pore size at the upper end of the filter section 32 and gas bubbles will remain at the upper end of the housing and will be purged through the purge tube 20. This will enable the higher density portion of the blood with a minimal quantity of gas bubbles therein to pass through the lower end of the filter section 32. Since the lower end has a higher pore size and a lower bubble point, the volumetric flow through the lower end will be significantly higher than that in the upper end of the filter section 32. Overall, the flow rate will increase. However, the lower density large size particulate matter and gas bubbles will be rejected by the filter 32 at the upper end thereof.

Referring now to FIG. 3, there is illustrated a cross-sectional diagram of an alternate embodiment of the present invention and FIG. 4 illustrates a top view thereof. The embodiment of FIGS. 3 and 4 are identical to the embodiment of FIGS. 1 and 2 with the exception that the upper housing 10 is replaced by an upper housing 10' having inlet 18' and forming an interior chamber 16'. The upper end of the upper housing 10' has a self-venting device disposed on the upper surface thereof. The self-venting device is comprised of a porous thermoplastic tube material which allows air bubbles in the upper end thereof to escape to provide the self-venting feature. A hydrophobic membrane 40 is disposed thereunder to separate the interior chamber 16' from the atmosphere. Gas bubbles can pass through the membrane 40 and then through the porous thermoplastic material 38 to provide the self-venting structure. This self venting structure is described in U.S. Pat. No. 4,572,724, which is incorporated herein by reference and has been commonly incorporated in medical devices for over twenty years.

Referring now to FIG. 5, there is illustrated a diagrammatic view of the air eliminator of FIGS. 1 and 2. The interior chamber 16 is generally defined by a housing 44. The interior chamber 24 is defined as being bounded by the filter section 32 on the sides thereof with an upper bounding surface 46. The filter section 32 is divided into four separate filter segments each with a different pore size and associated bubble point. There is a first filter segment 48 disposed on the upper end of the filter section 32. In a similar manner, a second filter segment 50 is disposed adjacent to filter segment 48 with a filter segment 52 disposed adjacent the filter segment 50 and a filter segment 54 disposed adjacent to filter segment 52. The pore sizes of the filter segments 48-54 increase from top to bottom with the pore size of filter segment 48 being, for example, 20 microns, the pore size of filter segment 50 being 40 microns, the pore size of filter segment 52 being 80 microns and the pore size of filter segment 54 being 120 microns. The bubble points decrease from a large value for filter segment 48 to a small valve for filter segment 54. Although the filter section 32 is illustrated as being comprised of four discrete filter sections, it should be understood that the filter section 32 could have a graduated configuration such that the pore size varies from the top to bottom in a progressive fashion from smaller to larger with the value of the bubble point progressively decreasing.

In operation, oxygenated blood enters the inlet tube 18 in the upper portion of the housing 44. As described above with reference to FIGS. 1 and 2, the inlet 18 is offset in the upper end of the housing 44, which housing 44 is cylindrical in shape, such that it swirls around in the upper end. A purge source is connected to the outlet tube 20 in the upper end of the housing 44 to remove a portion of the fluid in the upper end of the housing 44. The fluid that moves toward the lower end of the housing 44 is first pulled through the filter section 48 in the upper end of the filter section 32, which filter section 48 rejects any particulate matter over 20 microns in size and any air bubbles regardless of size. This will typically result in rejection of air bubbles and the such. Since these air bubbles have a lower density, they will tend to remain at the top portion of the chamber 16. The lower density material will move toward the bottom and particulate matter larger than 40 microns will be rejected by filter section 50, particulate matter greater than 80 microns will be rejected by filter section 52 and particulate material greater than 120 microns will be rejected by filter section 54. It should be noted that the region proximate to the filter section 48 in the interior chamber 16 will have a higher concentration of particulate matter having a size greater than 20 microns since that portion of the oxygenated blood with a size less than 20 microns will pass through the filter section 48 to the interior chamber 24. In the portion of the interior chamber 24 proximate to the filter section 48, there will be virtually no particulate matter greater than 20 microns and no gas bubbles present. In a similar manner, filter section 50 in chamber 16 proximate thereto will have a relatively high concentration of particulate matter with a size greater than 40 microns. The interior chamber 24 in a region proximate to the filter section 50 will have a relatively high concentration of particulate matter less than 40 microns. This will continue in the same manner with respect to filter sections 52 and 54. Due to the density of the material, particulate matter of a large pore size and a low density and gas bubbles will tend to gravitate toward the upper end of the housing 44. With the help of the purge tube 20, this particulate matter and gas bubbles can be siphoned off of the upper portion of the interior chamber 16 such that it will not be allowed to gravitate downward to the filter section 54. The only material that will filter down to the filter section 54 is that portion of the higher density 20 micron, 40 micron, 80 micron and 120 micron that was not of such a density as to remain in the upper portion of the housing 44. Therefore, if the flow rate is sufficient, the higher density 20 micron–120 micron particulate matter such as blood, etc. will pass through the filter section 54. One advantage to this operation is that flow of particulate matter having a size less than 120 microns will flow through filter section 54 at a faster rate than through filter section 48. Therefore, the use of the graduated pore size and bubble point in the filter section 32 allows a higher throughput as compared to a filter section with a single uniform pore size and bubble point. Of course, if the flow rate increases beyond a certain point, the lower density materials such as the microbubbles will be pulled downward and through the filter section 54. Therefore, the flow rate must be experimentally determined so as to maintain the high concentration of the lower density large particulate matter in the upper end of the housing 44.

Referring now to FIG. 6, there is illustrated an expanded view of the filter section 32, illustrated as a flat sheet. The filter section 32 has a side edge 56 and a side edge 58. The side edges 56 and 58 are operable to be joined together. The material is comprised of a polyester screen wherein polyester strands are woven to form the pore openings of the filter screen. The polyester material can be heat welded to form a seam along the edges 56 and 58 to provide a cylindrical configuration. In a similar manner, separate sheets of filter screen material are utilized for the filter segments 48, 50, 52 and 54. Therefore, the one edge of each of the filter segments 48 and 50 are heat welded together to form a seam 60, one edge of the filter material in filler segments 50 and 52 are heat welded together to form a seam 62 and one edge of the filter material in filler segments 52 and 54 are heat welded together to form a seam 64.

Referring now to FIG. 7, after the cylindrical shape is formed by heat welding edges 56 and 58 together, a seam 66 is formed. FIG. 7 illustrates a top view wherein the filter section 32 is then configured in a pleated form to increase the surface area for a given cylindrical dimension.

Referring now to FIG. 8, there is illustrated an alternate embodiment of the present invention. A housing 68 is formed having an inlet 70 and a purge outlet 72 in the upper end thereof. The housing 68 is similar to the housing 44 of FIG. 5 with the diagram of FIG. 8 providing a diagrammatic view of the operation. The housing 68 has a first chamber 74 formed proximate to the interior walls thereof with a second chamber 76 formed within a filter section 78. Chamber 74 is similar to the chamber 16 and the chamber 76 is similar to the chamber 24. Filter section 78 is similar to the filter section 32. The filter section 78 is cylindrical in shape and has on the upper surface thereof a sealing member 80 and the lower peripheral edges of the filter 78 abut the lower surface of the housing 68 to form a seal therewith. The filter section 78 is comprised of four graduated segments 82, 84, 86 and 88, which are similar to filter segments 48, 50, 52 and 54 respectively. As described above, each of the filter sections 82–88 is comprised of a material having different porosities and different bubble points, with the filter segment 82 having a lower pore size and higher bubble point than the filter segment 88 which, in the preferred embodiment, is graduated from 20 microns to 120 microns.

Four taps 90, 92, 94 and 96 are provided between the interior of the chamber 76 and the exterior of the housing 68. The tap 90 has the inlet side thereof disposed proximate to the filter segment 82. The tap 92 has the inlet side thereof disposed proximate to the filter segment 84. The tap 94 has the inlet side thereof disposed proximate to the filter segment 86. The tap 96 has the inlet side thereof disposed proximate to the filter segment 88. Therefore, the taps 90–96 provide a chamber operation wherein the tap 90 can divert fluid material that is essentially comprised of material that will pass through the filter segment 82. In a similar manner, the tap 92 will remove fluid that passes through the filter segment 84 with some fluid that has passed through the segment 82. Tap 94 will divert fluid that is predominantly comprised of the fluid passing through the filter segment 86 with some fluid from the filter segments 82 and 84. Tap 96 will divert fluid primarily composed of that passing through filter segment 88.

Figure 9:
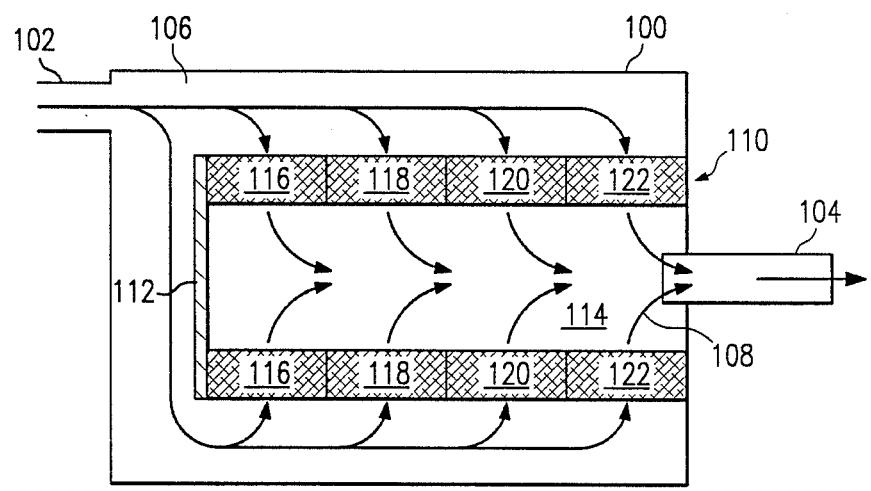
FIG. 9 illustrates an alternate embodiment of the present invention operable in the horizontal orientation.

Referring now to FIG. 9, there is illustrated an alternate embodiment of the structure of FIG. 5 which comprises a diagrammatic view. The housing 100 is cylindrical in shape with sealed ends and disposed with the longitudinal axis thereof in a horizontal orientation. An inlet 102 is provided on one end and an outlet 104 is provided on the opposite end. An interior chamber 106 is formed proximate to the interior sides of the housing 100 and an interior chamber 108 is formed interior to the chamber 106 and separated therefrom by a filter section 110. The filter section 110 is cylindrical in shape with an upper sealing surface 112 diametrically opposite to the output 104 with the opposite end of the filter section 110 on the peripheral edges thereof disposed adjacent the end of housing 100 in which the outlet 104 is formed to form a seal therewith. This results in a chamber 114 being defined therein. The filter section 110 is comprised of four filter segments, 116, 118, 120 and 122, each having a different pore size and associated bubble point.

In operation, the fluid enters in the inlet tube 102 and flows along the surface of the filter 110 with the filter segments 116–122 each discriminating as to what portion of the combined fluid and gas bubbles passes therethrough. Since the filter segments are disposed along the flow path thereof, the filter segment 116 provides the first discrimination operation whereas the filter segment 122 provides the last discrimination operation. In this manner, discrimination is made with respect to the flow rate of particulate matter and the gas bubble content.

Although the preferred embodiment has been described in detail, it should be understood that various changes, substitutions and alterations can be made therein without departing from the spirit and scope of the invention as defined by the appended claims.

I claim:

1. An air eliminator for blood, comprising:
   an outer housing having an upper end and a lower end;
   an inlet formed in the upper end of said housing;
   an outlet formed in the lower end of said housing;
   an interior housing between said inlet from said outlet to form a first interior chamber on one side of a filter element for receiving fluid and associated gas bubbles from said inlet and forming a second interior chamber on the other side of the filter element for outputting fluid to said outlet, said interior housing having at least one substantially vertical surface between said first and second interior chambers and having an upper end and a lower end;
   the filter element formed on a portion of said substantially vertical surface for allowing fluid to flow between said first and second interior chambers, said filter element having a bubble point that decreases from a predetermined maximum value at the upper end thereof to a predetermined minimum value at the lower end thereof wherein said filter element has a pore size that decreases from a predetermined minimum size at the upper end thereof to a predetermined maximum size at the lower end thereof; and
   purge means for eliminating the portion of the fluid and associated gas bubbles in the upper end of said housing.

2. The air eliminator of claim 1 wherein said filter element is pleated to increase the surface area thereof.

3. The air eliminator of claim 1 wherein said filter material with an associated bubble point is comprised of a plurality of layers of filter element, each layer having an upper edge and a lower edge and disposed in an adjacent relationship such that the bubble point incrementally decreases from one of said layers of filter material to the next adjacent one thereof with the lower peripheral edge of each of the layers of filter material being adhered to the upper edge of the next adjacent one, with the upper end of the first of said layers of filter material with the largest bubble point comprising the upper end of said filter element and the one of the largest pore size of said layers of filter material with the smallest bubble point comprising the lower end of said filter element.

4. The air eliminator of claim 1 wherein the outer surface of said filter element tapers downward and outward from the upper end to the lower end of said housing.

5. The air eliminator of claim 1 wherein said purge means comprises a purge tube disposed in the upper end of said housing for being connected to a purge medium that removes the portion of the blood and gas bubbles in the upper end of said housing therefrom.

6. The air eliminator of claim 5 wherein a portion of the upper end of said housing is comprised of a frusto-conical shaped chamber with the upper end of said frusto-conical shaped chamber having an outlet formed therein to comprise said purge tube.

* * * * *